United States Patent [19]

Cartmell et al.

[11] Patent Number: 5,531,999
[45] Date of Patent: Jul. 2, 1996

[54] ROPE-SHAPED WOUND DRESSING

[75] Inventors: James V. Cartmell, Xenia; Wayne R. Sturtevant, Centerville; Michael L. Wolf, West Milton; Michael J. Allaire, Cincinnati, all of Ohio

[73] Assignee: NDM, Inc., Utica, N.Y.

[21] Appl. No.: 810,685

[22] Filed: Dec. 19, 1991

[51] Int. Cl.⁶ ..................................................... A61F 13/00
[52] U.S. Cl. .......................................... 424/445; 424/443
[58] Field of Search .................................. 424/443, 445; 128/152, 155, 156; 604/368, 385.1

[56] References Cited

U.S. PATENT DOCUMENTS

| | | | |
|---|---|---|---|
| 4,226,232 | 10/1980 | Spence | 128/156 |
| 4,361,151 | 11/1982 | Fitzgerald | 604/368 |
| 4,377,160 | 3/1983 | Romaine | 128/156 |
| 4,393,048 | 7/1983 | Mason, Jr. et al. | 128/156 |
| 4,517,326 | 5/1985 | Cordts et al. | 521/310 |
| 4,657,006 | 4/1987 | Rawlings et al. | 128/156 |
| 4,770,299 | 9/1988 | Parker | 206/409 |
| 4,867,821 | 9/1989 | Morgan | 156/152 |
| 4,891,263 | 1/1990 | Kotliar et al. | 428/225 |
| 4,899,738 | 2/1990 | Parker | 128/90 |
| 4,909,244 | 3/1990 | Quarfoot et al. | 128/156 |
| 4,911,155 | 3/1990 | Delannoy | 128/155 |
| 4,916,193 | 4/1990 | Tang et al. | 525/413 |
| 4,920,158 | 4/1990 | Murray et al. | 523/111 |
| 5,003,970 | 4/1991 | Parker et al. | 128/90 |
| 5,006,401 | 4/1991 | Frank | 428/231 |
| 5,013,769 | 5/1991 | Murray et al. | 523/111 |
| 5,025,783 | 6/1991 | Lamb | 128/156 |
| 5,059,424 | 10/1991 | Cartmell et al. | 424/443 |
| 5,154,706 | 10/1992 | Cartmell et al. | 604/307 |

FOREIGN PATENT DOCUMENTS

| | | |
|---|---|---|
| 48769/90 | 1/1990 | Australia. |
| 863300 | 5/1978 | Belgium. |
| 0426422 | 5/1991 | European Pat. Off.. |
| 2367/80 | 11/1980 | Israel. |

Primary Examiner—Jyothsna Venkat
Attorney, Agent, or Firm—Killworth, Gottman, Hagan & Schaeff

[57] ABSTRACT

The present invention provides a hydrogel wound dressing substantially in the form of a rope and also in the form of a strand. The wound dressing comprises a hydrogel material substantially in a rope configuration or a strand configuration having a predetermined length for filling the cavity of a wound, and a dressing removal layer disposed within the strand configuration. The dressing removal layer may extend outwardly from an end so as to form a pull tab which facilitates removal of the rope configuration from the wound. The present invention also provides a wound dressing comprising a hydrogel material substantially in a strand configuration having a predetermined length for filling the cavity of a wound. The strand configuration also includes a dressing removal layer disposed within the strand configuration and may also include a pull tab which facilitates removal of the strand configuration from the wound.

20 Claims, 3 Drawing Sheets

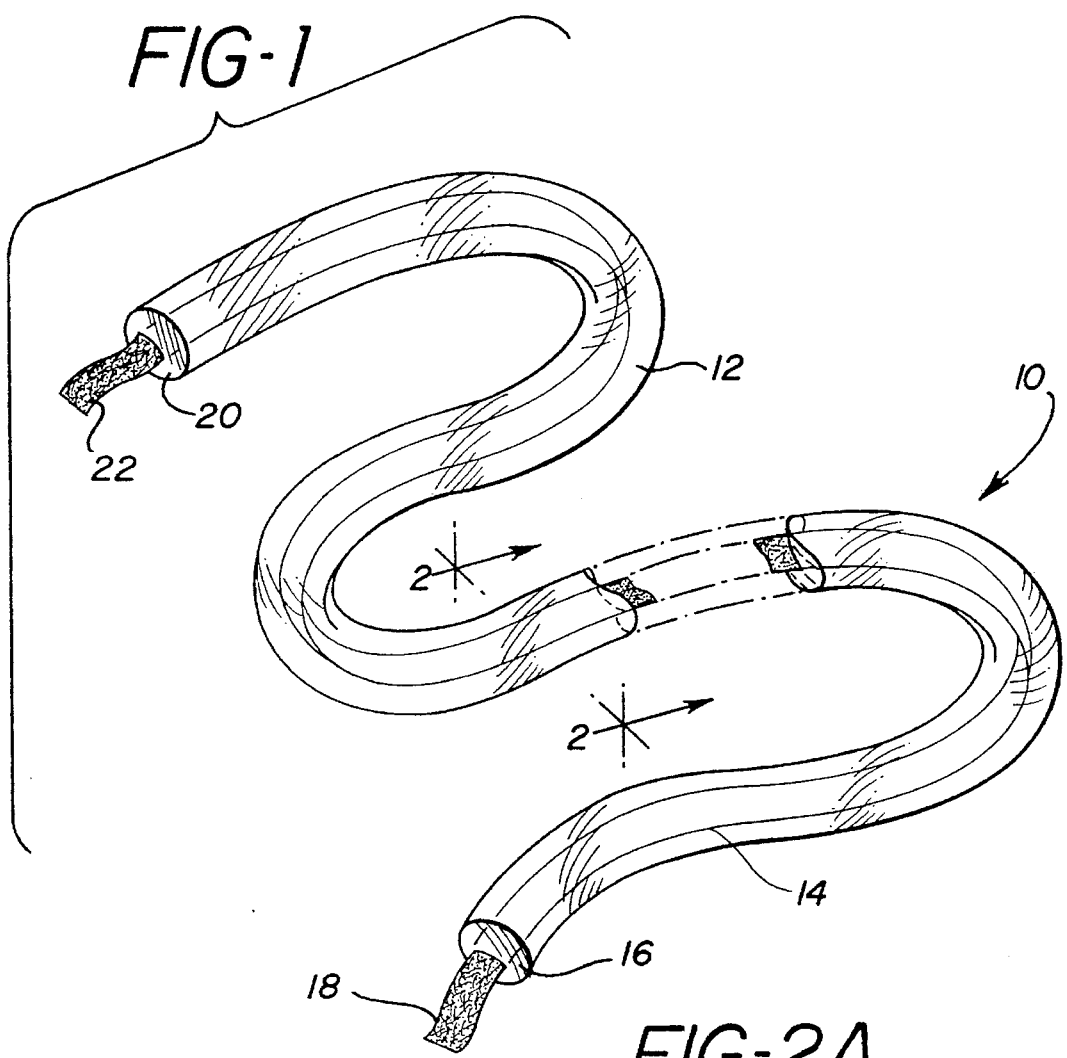
FIG-1
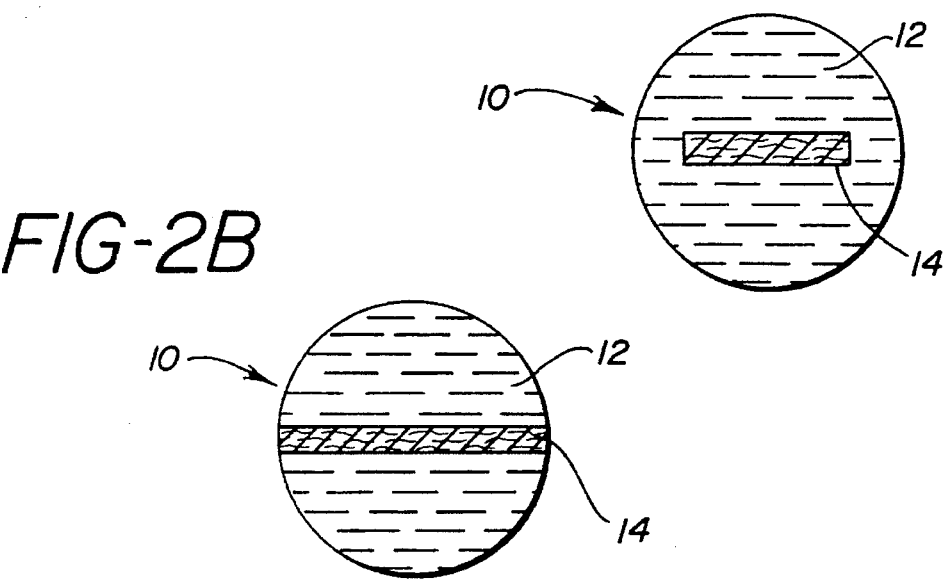
FIG-2A
FIG-2B

ROPE-SHAPED WOUND DRESSING

BACKGROUND OF THE INVENTION

The present invention generally relates to wound dressings and, more particularly, to a wound dressing comprising a hydrogel material substantially in a rope configuration or in a strand configuration and a dressing removal layer disposed therein.

Secreting skin wounds, such as decubitus ulcers and open surgical wounds, have long presented a medical challenge in keeping such wounds sterile and relatively dry. The accumulation of wound exudate, such as blood, pustulation, and other wound fluids, in wound crevices promotes growth of bacteria and crusted organisms which cause infection and delay the healing process. Such wound exudate may also cause maceration of tissue adjacent the wound and support infection thereof. However, since it is often desirable to allow a wound to heal in a slightly "moist" or occlusive state which is believed to accelerate healing, excess wound exudate must be removed. If excess wound exudate remains on a wound, a "blister" of exudate can form under the wound dressing which is not only unsightly, but also may cause the dressing to leak, thereby defeating the aim of sterility. However, existing methods of aspiration can lead to wound infection or can destroy sterility. Additionally, it is not desirable to remove all the exudate as that would result in a "dry" wound resulting in a slower healing process.

The art is replete with wound and/or surgical dressings for treating skin lesions, such as decubitus ulcers and open surgical wounds. For example, Mason, Jr. et al, U.S. Pat. No. 4,393,048, disclose a hydrogel wound treatment composition which dries to a powder after it is introduced into an open, draining wound to absorb wound exudate. However, dry hydrogel deteriorates as the wound fluids are absorbed resulting in lumping and uneven application. Additionally, such deteriorated lumps are difficult to remove from a wound site without damaging new cell tissue at the wound site. Furthermore, the progress of wound healing cannot be determined without removing, at least partially, the wound dressing from the wound site.

Aqueous moisture absorbing materials, such as a hydrogel material with a polyethylene glycol liquid curing agent as disclosed in Spence, U.S. Pat. No. 4,226,232, are easier to remove from the wound site, but cannot be sterilized by irradiation due to the formation of free radicals within the aqueous material. Another aqueous absorbing material used to absorb wound exudate is an hydrophilic polymer as disclosed in Rawlings et al, U.S. Pat. No. 4,657,006. Rawlings et al disclose a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound, thereby providing an excellent environment for bacteria proliferation.

Nor are existing wound dressings conducive for healing wounds which extend well below the surface of the skin. In fact, it is not uncommon for certain wounds to extend down to the bones or tendons. However, known wound dressings do not facilitate the healing of such wounds as exemplified by the wound dressings in Mason, Jr. et al, Spence, and Rawlings et al which are designed for treating surface wounds. Moreover, filler gel packs which have been used to temporarily fill wounds tend to break apart into fragments upon removal from the wound. These filler gel packs are also difficult to wash out from the healing wound since there is a tendency for the filler material to adhere to the new cell tissue forming on the surface of the wound.

Accordingly, there is a need for a wound dressing especially conducive for wounds which penetrate the surface of the skin. There is also a need for a wound dressing for a wound which may be precut, sterilized, and readily available for application to a draining wound and which contains an exudate absorbing composition. Finally, there is a need for a wound dressing which may be removed from the wound neatly as a single piece without adhering to the new cell tissue of the wound.

SUMMARY OF THE INVENTION

The present invention meets the aforementioned needs by providing a wound dressing in a form which facilitates the disposal and removal of the wound dressing from wounds found on patients. The wound dressing is made from a hydrogel material which is especially conducive for wound healing and for promoting new cell tissue formation in that it absorbs large amounts of bodily fluids, such as wound exudate, yet does not break apart into pieces or fragments upon removal from the wound in which the wound dressing is disposed. The invention contemplates a wound dressing substantially in a rope configuration and a wound dressing substantially in a strand configuration. The term rope as used herein is defined as an elongated flexible cable or cord generally having a circular or elliptical cross-section. Additionally, the term strand as used herein is defined as an elongated flexible ribbon or cord having a substantially rectangular or square shaped cross-section.

In accordance with one aspect of the present invention, the wound dressing comprises a hydrogel material configured substantially in a rope configuration having two ends and a predetermined length for filling the cavity of a wound. The hydrogel material is formed from a mixture comprising: (a) from about 0% to about 90% by weight polyhydric alcohol; (b) from about 6% to about 60% by weight isophoronediisocyanate terminated prepolymer; (c) from about 4% to about 40% by weight polyethylene oxide based diamine; (d) up to about 2% by weight sodium chloride; and (e) the balance water. A dressing removal layer is disposed within the rope configuration extending outwardly from an end of the rope configuration so as to form a pull tab which facilitates removal of the rope configuration from the wound substantially as a single piece.

In accordance with another aspect of the invention, the wound dressing comprises a hydrogel material configured substantially in a strand configuration having two ends and a predetermined length for filling the cavity of a wound. The hydrogel material is formed from a mixture comprising: (a) from about 0% to about 90% by weight polyhydric alcohol; (b) from about 6% to about 60% by weight isophoronediisocyanate terminated prepolymer; (c) from about 4% to about 40% by weight polyethylene oxide based diamine; (d) up to about 2% by weight sodium chloride; and (e) the balance water. The wound dressing further includes a dressing removal layer disposed within the strand configuration. The dressing removal layer may extend outwardly from an end of the strand configuration so as to form a pull tab which facilitates removal of the strand configuration from the wound substantially as a single piece.

Accordingly, it is an object of the present invention to provide a wound dressing especially conducive for wounds which penetrate the surface of the skin; to provide a wound dressing for a wound which may be precut, sterilized, and readily available for application to or into a draining wound and which contains an exudate absorbing composition; and to provide a wound dressing which may be removed from the wound neatly as a single piece without adhering to the new cell tissue of the wound. Other objects and advantages of the invention will be apparent from the following detailed description, the accompanying drawings and the appended claims.

BRIEF DESCRIPTION OF THE DRAWINGS

FIG. 1 is a perspective view of the wound dressing in accordance with the invention;

FIGS. 2A and 2B are cross-sectional views of the wound dressing taken along view line 2—2 in FIG. 1;

DETAILED DESCRIPTION OF THE PREFERRED EMBODIMENT

Figure 3:
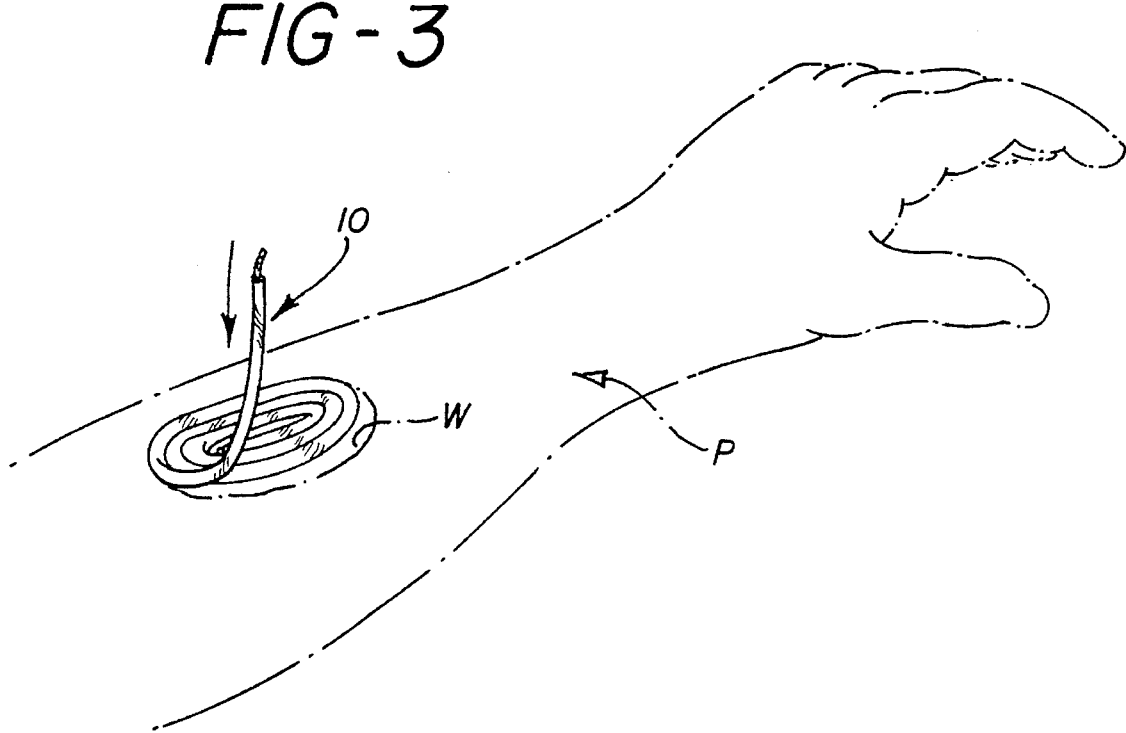
FIG. 3 is a perspective view of the wound dressing illustrated in FIG. 1 being systematically disposed within a wound found on a patient.

The present invention relates to wound dressing 10 as seen in the perspective view of FIG. 1. The wound dressing 10 preferably comprises a hydrogel material substantially in a rope configuration 12 having a predetermined length for filling the cavity of a wound W (FIG. 3). As stated previously, the term rope as used herein is defined as an elongated flexible cable or cord generally having a circular or elliptical cross-section. The hydrogel material 12 used to form the rope configuration 12 is a tacky, flexible material capable of absorbing bodily fluids such as wound exudate, perspiration and the like without breaking apart into fragments. Furthermore, the preferred hydrogel material also provides a biocompatible, non-irritating, fluid absorbing, bacterial protective, cushioning media for application to the wound site. Thus, the hydrogel material is especially conducive for healing wounds found on a patient P.

A dressing removal layer 14 is disposed within the rope configuration 12 which extends outwardly from an end 16 so as to form a pull tab 18 which facilitates removal of the wound dressing 10 from the wound W. The pull tab 18 facilitates removal of the wound dressing 10 since it provides a means for pulling the wound dressing 10 out from the wound W. It should be understood, however, that the dressing removal layer 14 does not have to extend .outwardly from the end 16. Those skilled in the art will appreciate that other means such as tweezers and the like may be used to remove the wound dressing 10 in that case. The dressing removal layer 14 may be provided for the sole purpose of providing support for the hydrogel within which the dressing removal layer 14 is disposed.

As those skilled in the art will appreciate, the dressing removal layer 14 may extend throughout the entire length of the rope configuration 12 and outwardly from an end 20 located opposite to the end 16 to form a second pull tab 22 so as to facilitate further the removal of the wound dressing 10 from the wound W. The ends 16 and 20 are also referred to herein as first and second ends, respectively, of the rope configuration 12. Those skilled in the art will appreciate that removal of the wound dressing 10 as a single piece is more conducive for the healing process since destruction of the new cell tissue in the wound W is minimized as the wound dressing 10 is removed. Such removal is accomplished more easily with the aforementioned pull tab 18 and/or tweezers and the like. The disposal and removal procedures are discussed more fully below.

Referring now collectively to FIGS. 2A and 2B, cross-sectional views of the wound dressing 10 are shown. As seen in FIGS. 2A and 2B, the hydrogel material surrounds dressing removal layer 14 which may extend to the outer edges of the wound dressing 10 (FIG. 2B) or be centrally positioned within the hydrogel material (FIG. 2A). It should be understood that the dressing removal layer 14 may be positioned at any depth within the rope configuration 12. Preferably, the dressing removal layer 14 is at a depth such that the entire wound dressing 10 can be removed from the wound W as a single piece by pulling the pull tab 18 or with tweezers or the like. The length of the wound dressing 10 will depend upon the size of the wound W and may be controlled by packaging the wound dressing 10 in a manner such that it may be cut to the desired length. For example, the wound dressing 10 may be spirally wrapped onto a spool which maybe easily accessed by pulling the rope configuration 12 out to the desired length and then, cutting it with a knife or the like. The particular thickness of the wound dressing 10 can vary depending on the particular application for which the wound dressing 10 is directed. The most prevalent thickness or cross-sectional diameter, however, will be in a range from about 3 mm to about 10 mm which will be sufficient for most wounds found on the patient P.

The healing of the wound W and the removal of the wound dressing 10 are especially facilitated by the particular hydrogel material used. The preferred hydrogel material is formed from a mixture of polyhydric alcohol, isophoronediisocyanate terminated prepolymer, polyethylene oxide based diamine, sodium chloride and water. Preferably, the polyhydric alcohol is selected from the group consisting of polypropylene glycol, polyethylene glycol and glycerine. By forming the hydrogel material from the aforementioned aqueous mixture, the wound dressing 10 remains intact as it absorbs wound exudate from the wound W. Furthermore, the hydrogel material does not adhere or stick to the wound W which allows for easy removal of the wound dressing 10 without causing damage to the new cell tissue forming in the wound W. In addition, the biocompatibility of the hydrogel material within the wound W is extremely favorable. All of these characteristics are especially conducive for the healing process of most wounds found on patients.

The preferred hydrogel material is formed from a mixture comprising from about 0% to about 90% by weight polyhydric alcohol; from about 6% to about 60% by weight isophoronediisocyanate terminated prepolymer; from about 4% to about 40% by weight polyethylene oxide based diamine; up to about 2% by weight sodium chloride; and the balance water. A more preferred mixture from which the hydrogel material is formed comprises including from about 15% to about 30% by weight polyhydric alcohol; from about 8% to about 14% by weight isophoronediisocyanate terminated prepolymer; from about 5% to about 10% by weight polyethylene oxide based diamine; up to about 1% by weight sodium chloride; and the balance water. Most preferably, the hydrogel material is from a mixture comprising:
(a) from about 16% to 17% by weight polypropylene glycol;
(b) from about 10% to 12% by weight isophoronediisocyanate terminated prepolymer; (c) from about 7% to 9% by weight polyethylene oxide based diamine; (d) about 0.5% to 1% by weight sodium chloride; and (e) the balance water.

The isophoronediisocyanate terminated polymer is preferably based on polyols containing more than about 40% polyethylene oxide and having an isocyanate content of about 3% by weight. The molecular weight is preferably in a range from 1500–8000 and most preferably, from about 4000 to 5000. The molecular weight of the polyethylene oxide based diamine is preferably in a range from about 200 to 6000 and most preferably, about 2000. Those skilled in the art will appreciate that all of the constituents which ultimately form the preferred hydrogel material may be readily synthesized or purchased commercially. The aforementioned preferred hydrogel material provides a wound dressing 10 having the desired properties of excellent biocompatibility and absorption of exudate properties without adhering to the wound W. However, other materials having such characteristics, including but not limited to the aforementioned hydrogel compositions, may be used to form the hydrogel layer 12 in accordance with the present invention.

Figure 4:
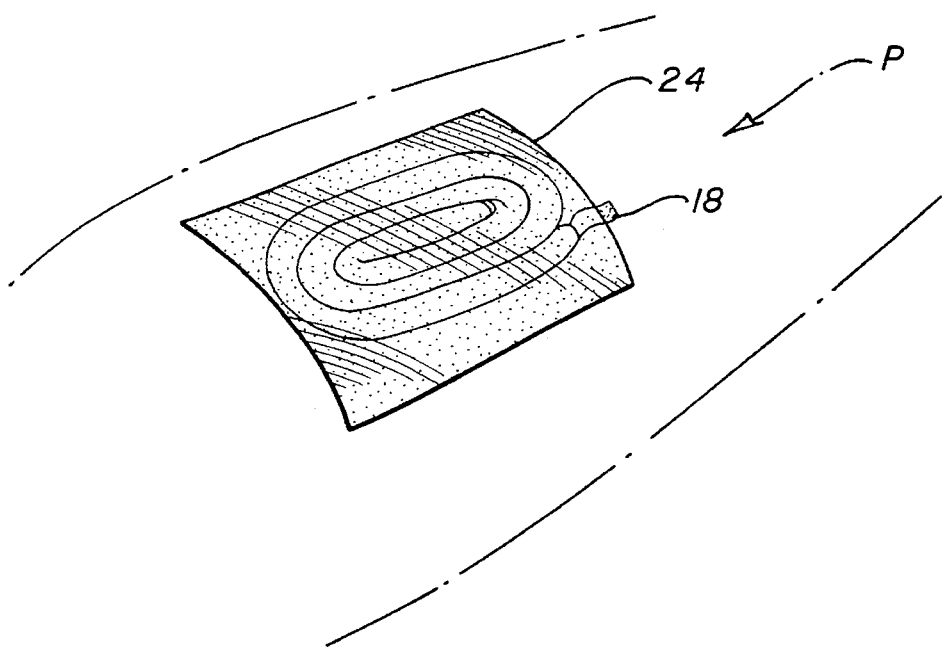
FIG. 4 is a perspective view of the wound dressing disposed within a wound and covered with a transparent protective layer.

The dressing removal layer 14 is preferably made from a material selected from the group consisting of scrim, fabrics, fiber nettings and combinations thereof. However, the material used to form the dressing removal layer 14 may include any material which can be characterized as flexible, non-toxic to the human body, and capable of adhering to the hydrogel material, even after a substantial amount of wound exudate has been absorbed into the wound dressing 10. As best seen in FIG. 4, the material must be flexible so as to allow the pull tab 18 and/or the pull tab 22 to be pulled away from the surface of the skin upon which it rests. It is preferable to use a non-toxic material to eliminate or minimize the likelihood of toxic poisoning through the skin or directly in the wound W. Additionally, the material must have the ability to adhere to the hydrogel material even when exposed to a substantial amount of wound exudate in order to permit the removal of the wound dressing 10. Therefore, any material in addition to the aforementioned materials may be used in accordance with the invention. Most preferably, the dressing removal layer is made from a fabric such as textured polyester or a scrim material.

The method of using the wound dressing 10 is best seen in FIGS. 3–4 collectively. The first step is illustrated in FIG. 3 which shows the wound dressing 10 being disposed systematically into the wound W found on the patient P. The wound dressing 10 is adapted for the wound W in that it will be cut to a length sufficient to fill the cavity of the wound W. Accordingly, the rope configuration 12 may be sold in standard length strips and then cut to the desired length. Alternatively, the rope configuration 12 may be stored on a spool or the like and then accessed to the desired length after which the pull tab 18 may be formed by skiving a sufficient amount of hydrogel material to expose the dressing removal layer 14. Those skilled in the art will appreciate that other means for accessing the wound dressing 10 may be used without departing from the scope of the invention.

The dressing removal layer 14 may include the pull tab 20 to facilitate removal from the wound W. As seen in FIGS. 3 and 4, the wound dressing 10 is disposed into the wound W of the patient P such that the wound dressing 10 substantially fills the cavity created by the wound W. A protective layer 24 formed of a film material may be placed over the wound dressing 10 to prevent any contaminants from seeping into the wound W while the wound W is in its healing stage. The protective layer 24 may be formed of any known material which may be disposed in the manner contemplated by the present invention. In addition, the protective layer 24 may be transparent so that the healing process may be monitored. For example, a transparent, adhesive-coated polyurethane film may be used as the protective layer 24 such that the wound W may be observed by medical personnel without removing the protective layer 24.

The hydrogel material in the wound dressing 10 continuously absorbs wound exudate which causes the entire wound dressing 10 to swell, thereby filling any void space within the cavity of the wound W. After the healing process has progressed sufficiently, the protective layer 24 is removed and thereafter, the wound dressing 10 is removed from the wound W by pulling the pull tab 18. Alternatively, the wound dressing 10 may be removed with tweezers or other similar apparatus. As stated previously, the wound dressing 10 is preferably removed neatly as a single piece, thereby minimizing the destruction of the healing wound. The exact time at which the wound dressing 10 is removed from the patient P is determined by the attending medical personnel and will vary depending upon the patient and the wound size. It should be appreciated, however, that the overall healing process of the wound W is enhanced by the use of the wound dressing 10.

The wound dressing 10 may be produced in a variety of ways including but not limited to those described herein. By way of example only, one method for producing the wound dressing 10 of the invention is to extrude the hydrogel material in the rope configuration 12 while simultaneously feeding the dressing removal layer 14 into the hydrogel material such that the dressing removal layer 14 is disposed within the rope configuration 12. The extrusion apparatus will have a length sufficient to allow the hydrogel material to cure which will vary depending upon the composition of the hydrogel material, as well as other process parameters such as temperature and pressure. Those skilled in the art will appreciate that a multitude of other methods may be used to produce the wound dressing 10 without departing from the scope of the invention.

Figure 5:
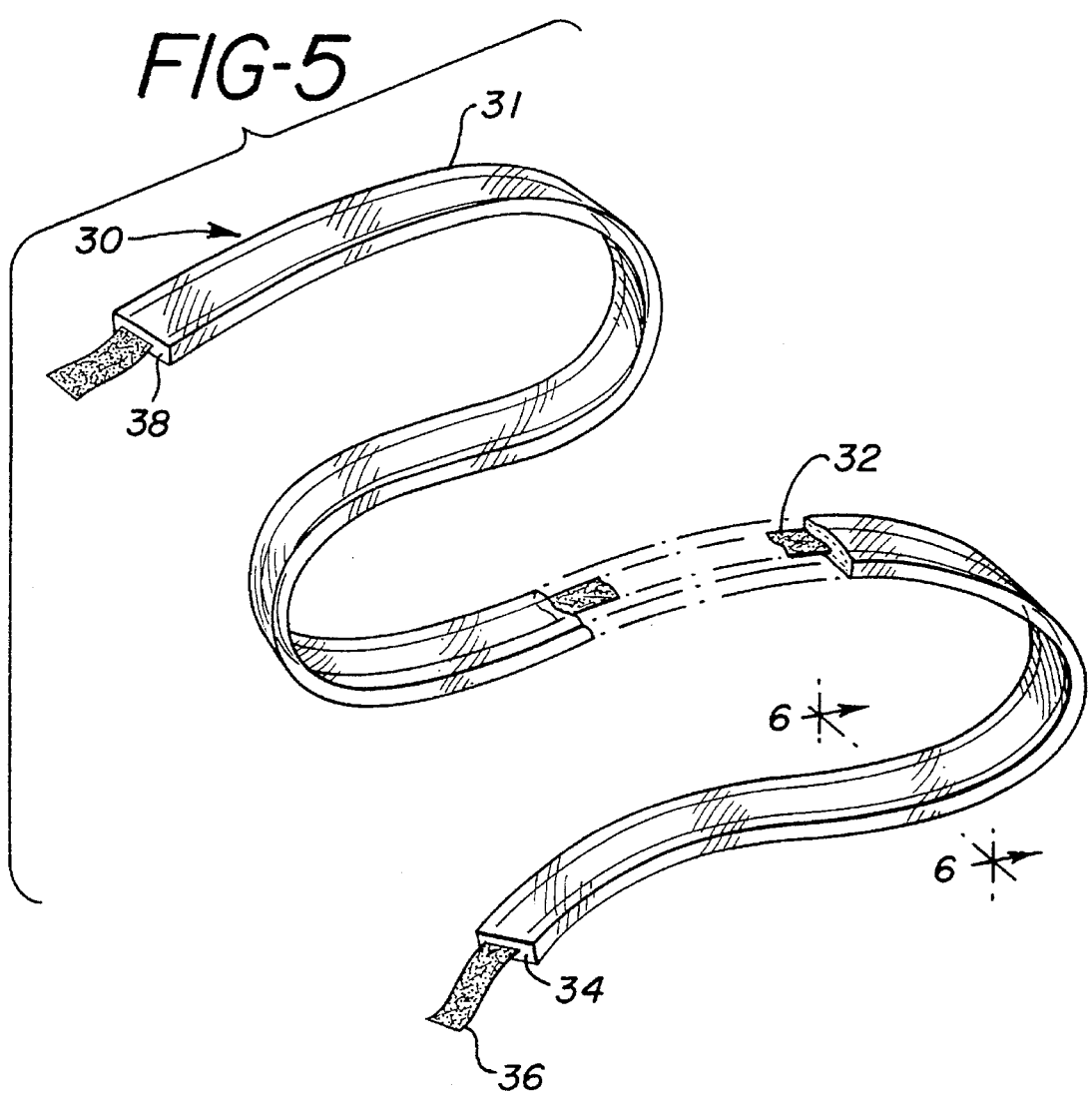
FIG. 5 is a perspective view of another embodiment of the wound dressing according to the invention.
Figure 6A:
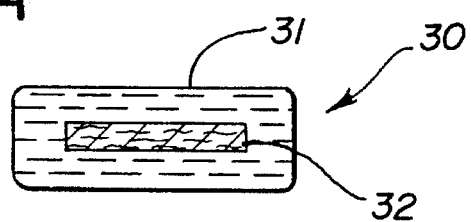
FIGS. 6A and 6B are cross-sectional views of the wound dressing shown in FIG. 5 taken along view line 6—6.
Figure 6B:
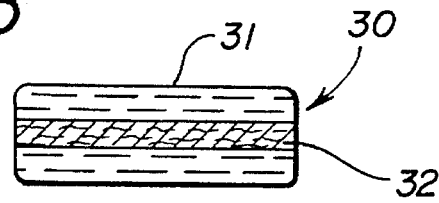

Referring collectively to FIGS. 5, 6A and 6B, another embodiment 30 of a wound dressing in accordance with the invention is illustrated. The wound dressing 30 includes the hydrogel material, as detailed above, substantially in the form of a strand configuration 31 having a predetermined length and thickness for filling the cavity of the wound W. As stated previously, the term strand as used to describe the strand configuration 31 is defined herein as an elongated flexible ribbon or cord having a substantially rectangular or square shaped cross-section. The hydrogel material surrounds dressing removal layer 32 which is disposed within the strand configuration 31 and can extend to the outer edges of the wound dressing 30 (FIG. 6B) or be disposed centrally within the wound dressing 30. The dressing removal layer 32 extends outwardly from an end 34 of the strand configuration 31 so as to form a pull tab 36 which facilitates removal of the strand configuration 31 from the wound W. The dressing removal layer 32 may extend throughout the length of the strand configuration 31 and optionally, may extend outwardly from an end 38 opposite the end 34 of the strand configuration 31 so as to facilitate further the removal of the strand configuration 31 from the wound W. As stated previously, the dressing removal layer 32 does not need to extend out of the wound dressing 30, but rather, can be provided for the sole purpose of providing support for the hydrogel material. The ends 34 and 38 are also referred to herein as first and second ends, respectively, of the strand configuration 31. As in the wound dressing 10, the dressing removal layer 32 of the wound dressing 30 is preferably made from a material selected from the group consisting of fabrics, fiber nettings, scrim and combinations thereof. Most preferably, the dressing removal layer 32 is made from a textured polyester or a scrim material.

While the cross-section of the wound dressing 30 is shown to be substantially rectangular, those skilled in the art will appreciate that the strand configuration 31 may have other cross-sectional shapes without departing from the scope of the invention. Preferably, the strand configuration 31 will have a thickness in a range from about 3 mm to about 10 mm. It should be understood, however, that the strand configuration 31 may have a variety of cross-section shapes as well as thicknesses.

The wound dressing 30 is disposed and removed from the wound W found on the patient P as shown in FIGS. 3–4. As with the wound dressing 10, the wound dressing 30 is preferably removed from the wound W as a single piece. In this way, damage to the new cell tissue forming in the wound W is minimized and pieces and fragments of the hydrogel material do not remain in the wound W to inhibit the healing of the wound W. As stated above, the hydrogel material of the strand configuration 31 preferably comprises the compositions discussed above with regard to the wound dressing 10. Accordingly, the wound dressing 30 includes a hydrogel material having the desired characteristics, such as excellent biocompatibility and absorption of exudate capabilities without adhering to the wound W. The wound dressing 30 may be accessed in the same manner in which the wound dressing 10 is accessed, as well as any other means which may be contemplated by those skilled in the art.

As with the wound dressing 10, the wound dressing 30 may be produced in a variety of ways included but not limited to those described herein. For example, the wound dressing 30 of the present invention may be formed by preparing two thin layers of the hydrogel material and the dressing removal layer 32, individually, and thereafter, laminating the aforementioned layers together such that the dressing removal layer 32 is positioned between the two hydrogel material layers. Those skilled in the art may use other methods for producing the wound dressing 30 without departing from the scope of the invention.

Having described the invention in detail and by reference to preferred embodiments thereof, it will be apparent that modifications and variations are possible without departing from the scope of the invention which is defined in the appended claims. For example, various other hydrogel formulations and dressing removal layer materials may be used in accordance with the wound dressing embodiments described herein without departing from the scope of the invention.

What is claimed is:

1. A wound dressing comprising:
   a hydrogel material substantially in the form of an elongated member having a predetermined length for filling the cavity of a wound, said hydrogel material capable of being removed from said wound substantially as a single piece; and
   a dressing removal layer disposed in and surrounded by said hydrogel material, said hydrogel material being impregnated in said dressing removal layer to thereby allow removal of said hydrogel material substantially as a single piece upon absorption of exudate emitted from said wound.

2. A wound dressing as claimed in claim 1 wherein said dressing removal layer extends outwardly from a first end of said member so as to form a pull tab which facilitates removal of said hydrogel material from said wound.

3. A wound dressing as claimed in claim 2 wherein said dressing removal layer extends throughout said length of said member and extends outwardly from a second end opposite said first end of said member so to facilitate further the removal of said member from said wound.

4. A wound dressing as claimed in claim 1 wherein said dressing removal layer is made from a material selected from the group consisting of fabrics, fiber nettings, scrim and combinations thereof.

5. A wound dressing as claimed in claim 1 wherein said dressing removal layer is made from a textured polyester.

6. A wound dressing comprising:
   a hydrogel material substantially in a strand having a predetermined length for filling the cavity of a wound, said hydrogel material capable of being removed from said wound substantially as a single piece; and
   a dressing removal layer disposed in and surrounded by said hydrogel material, said hydrogel material being impregnated in said dressing removal layer to thereby allow removal of said hydrogel material substantially as a single piece upon absorption of exudate emitted from said wound.

7. A wound dressing as claimed in claim 6 wherein said dressing removal layer extends outwardly from a first end of said strand so as to form a pull tab which facilitates removal of said hydrogel material from said wound.

8. A wound dressing as claimed in claim 6 wherein said dressing removal layer extends throughout said length of said strand and extends outwardly from a second end opposite said first end of said strand so to facilitate further the removal of said strand from said wound.

9. A wound dressing as claimed in claim 6 wherein said dressing removal layer is made from a material selected from the group consisting of fabrics, fiber nettings, scrim and combinations thereof.

10. A wound dressing as claimed in claim 6 wherein said dressing removal layer is made from a textured polyester.

11. A wound dressing comprising:
    a hydrogel material substantially in the form of an elongated member having first and second ends and a predetermined length for filling the cavity of a wound wherein said hydrogel material is formed from a mixture comprising:
    (a) from about 0% to about 90% by weight polyhydric alcohol;
    (b) from about 6% to about 60% by weight isophoronediisocyanate terminated prepolymer;
    (c) from about 4% to about 40% by weight polyethylene oxide based diamine;
    (d) up to about 2% by weight sodium chloride; and
    (e) the balance water; and
    a dressing removal layer disposed in said hydrogel material, said hydrogel material being impregnated in said dressing removal layer to thereby allow removal of said hydrogel material substantially as a single piece upon absorption of exudate emitted from said wound, said removal layer extending outwardly from said first end of said member so as to form a pull tab which facilitates removal of said member from said wound substantially as a single piece.

12. A wound dressing comprising:
    a hydrogel material substantially in a strand having first and second ends and a predetermined length for filling the cavity of a wound wherein said hydrogel material is formed from a mixture comprising:
    (a) from about 0% to about 90% by weight polyhydric alcohol;

(b) from about 6% to about 60% by weight isophoronediisocyanate terminated prepolymer;
(c) from about 4% to about 40% by weight polyethylene oxide based diamine;
(d) up to about 2% by weight sodium chloride; and
(e) the balance water; and a dressing removal layer disposed in said hydrogel material, said hydrogel material being impregnated in said dressing removal layer to thereby allow removal of said hydrogel material substantially as a single piece upon absorption of exudate emitted from said wound, said removal layer extending outwardly from said first end of said strand so as to form a pull tab which facilitates removal of said strand from said wound substantially as a single piece.

13. A wound dressing comprising:

a hydrogel material substantially in the form of an elongated member having a predetermined length for filling the cavity of a wound, said hydrogel material capable of being removed from said wound substantially as a single piece, said hydrogel material comprising an aqueous mixture of polyhydric alcohol, isophoronediisocyanate terminated prepolymer, polyethylene oxide based diamine and sodium chloride; and a dressing removal layer disposed in said hydrogel material, said hydrogel material being impregnated in said dressing removal layer to thereby allow removal of said hydrogel material substantially as a single piece upon absorption of exudate emitted from said wound.

14. A wound dressing as claimed in claim 13 wherein said polyhydric alcohol is selected from the group consisting of polypropylene glycol, polyethylene glycol and glycerine.

15. A wound dressing comprising:

a hydrogel material substantially in the form of an elongated member having a predetermined length for filling the cavity of a wound, said hydrogel material capable of being removed from said wound substantially as a single piece, said hydrogel material comprising
(a) from about 0% to about 90% by weight polyhydric alcohol;
(b) from about 6% to about 60% by weight isophoronediisocyanate terminated prepolymer;
(c) from about 4% to about 40% by weight polyethylene oxide based diamine;
(d) up to about 2% by weight sodium chloride; and
(e) the balance water; and a dressing removal layer disposed in said hydrogel material, said hydrogel material being impregnated in said dressing removal layer to thereby allow removal of said hydrogel material substantially as a single piece upon absorption of exudate emitted from said wound.

16. A wound dressing comprising:

a hydrogel material substantially in the form of an elongated member having a predetermined length for filling the cavity of a wound, said hydrogel material capable of being removed from said wound substantially as a single piece, said hydrogel material comprising
(a) from about 15% to about 30% by weight polyhydric alcohol;
(b) from about 8% to about 14% by weight isophoronediisocyanate terminated prepolymer;
(c) from about 5% to about 10% by weight polyethylene oxide based diamine;
(d) up to about 1% by weight sodium chloride; and
(e) the balance water; and a dressing removal layer disposed in said hydrogel material, said hydrogel material being impregnated in said dressing removal layer to thereby allow removal of said hydrogel material substantially as a single piece upon absorption of exudate emitted from said wound.

17. A wound dressing comprising:

a hydrogel material substantially in a strand having a predetermined length for filling the cavity of a wound, said hydrogel material capable of being removed from said wound substantially as a single piece, said hydrogel material comprising an aqueous mixture of polyhydric alcohol, isophoronediisocyanate terminated prepolymer, polyethylene oxide based diamine and sodium chloride; and a dressing removal layer disposed in said hydrogel material, said hydrogel material being impregnated in said dressing removal layer to thereby allow removal of said hydrogel material substantially as a single piece upon absorption of exudate emitted from said wound.

18. A wound dressing as claimed in claim 17 wherein said polyhydric alcohol is selected from the group consisting of polypropylene glycol, polyethylene glycol and glycerine.

19. A wound dressing comprising:

a hydrogel material substantially in a strand having a predetermined length for filling the cavity of a wound, said hydrogel material capable of being removed from said wound substantially as a single piece, said hydrogel material comprising
(a) from about 0% to about 90% by weight polyhydric alcohol;
(b) from about 6% to about 60% by weight isophoronediisocyanate terminated prepolymer;
(c) from about 4% to about 40% by weight polyethylene oxide based diamine;
(d) up to about 2% by weight sodium chloride; and
(e) the balance water; and a dressing removal layer disposed in said hydrogel material, said hydrogel material being impregnated in said dressing removal layer to thereby allow removal of said hydrogel material substantially as a single piece upon absorption of exudate emitted from said wound.

20. A wound dressing comprising:

a hydrogel material substantially in a strand having a predetermined length for filling the cavity of a wound, said hydrogel material capable of being removed from said wound substantially as a single piece, said hydrogel material comprising
(a) from about 15% to about 30% by weight polyhydric alcohol;
(b) from about 8% to about 14% by weight isophoronediisocyanate terminated prepolymer;
(c) from about 5% to about 10% by weight polyethylene oxide based diamine;
(d) up to about 1% by weight sodium chloride; and
(e) the balance water; and a dressing removal layer disposed in said hydrogel material, said hydrogel material being impregnated in said dressing removal layer to thereby allow removal of said hydrogel material substantially as a single piece upon absorption of exudate emitted from said wound.

* * * * *